(12) United States Patent
Akhavan-Tafti

(10) Patent No.: US 8,012,705 B2
(45) Date of Patent: Sep. 6, 2011

(54) NONSEPARATION ASSAY METHODS

(75) Inventor: Hashem Akhavan-Tafti, Howell, MI (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 13/083,195

(22) Filed: Apr. 8, 2011

(65) Prior Publication Data

US 2011/0183361 A1     Jul. 28, 2011

Related U.S. Application Data

(60) Continuation of application No. 12/794,658, filed on Jun. 4, 2010, now Pat. No. 7,923,213, which is a division of application No. 11/799,895, filed on May 3, 2007, now Pat. No. 7,732,153.

(60) Provisional application No. 60/798,839, filed on May 9, 2006.

(51) Int. Cl.
*G01N 33/53* (2006.01)

(52) U.S. Cl. ............ 435/7.21; 435/2; 435/7.1; 436/501; 436/518; 436/522; 422/50; 530/300; 530/350

(58) Field of Classification Search ........................ None
See application file for complete search history.

(56) References Cited

U.S. PATENT DOCUMENTS

| | | | | |
|---|---|---|---|---|
| 4,161,515 A | * | 7/1979 | Ullman | 436/537 |
| 6,030,803 A | * | 2/2000 | Jacquemijns et al. | 435/28 |
| 6,613,578 B1 | * | 9/2003 | Moller et al. | 436/172 |
| 7,732,153 B2 | * | 6/2010 | Akhavan-Tafti | 435/7.21 |
| 7,923,213 B2 | * | 4/2011 | Akhavan-Tafti | 435/7.21 |

* cited by examiner

*Primary Examiner* — Lisa Cook
(74) *Attorney, Agent, or Firm* — Richard S. Handley

(57) ABSTRACT

Assay methods are disclosed involving specific binding reactions which are simplified compared to known methods. A compound capable of producing chemiluminescence is immobilized on a solid support as is a member of a specific binding pair for capturing an analyte from a sample. An activator compound that activates the chemiluminescent compound and is conjugated to a specific binding pair member is added in excess along with the sample to the solid support. Addition of a trigger solution causes a chemiluminescent reaction at the sites where the activator conjugate has been specifically bound. The assay methods are termed nonseparation assays because they do not require removal or separation of excess detection label (activator conjugate) prior to the detection step. The methods are applicable to various types of assays including immunoassays, receptor-ligand assays and nucleic acid hybridization assays.

17 Claims, 7 Drawing Sheets

NONSEPARATION ASSAY METHODS

CROSS-REFERENCE TO RELATED APPLICATION

The present application is a Continuation of U.S. application Ser. No. 12/794,658 filed Jun. 4, 2010, which is a Divisional of Non-Provisional application Ser. No. 11/799,895 filed on May 3, 2007, now U.S. Pat. No. 7,732,153, Issued Jun. 8, 2010, which claims the benefit of Provisional application Ser. No. 60/798,839 filed on May 9, 2006.

FIELD OF THE INVENTION

The present invention relates to novel assay methods involving specific binding reactions which are simplified compared to known methods. The assay methods are termed non-separation assays because they do not require removal or separation of excess detection label prior to the detection step. The methods are applicable to various types of assays including immunoassays, receptor-ligand assays and nucleic acid hybridization assays.

BACKGROUND OF THE INVENTION

A huge effort has been expended in the field of assay development, in particular in immunoassay development to simplify the design of assays while preserving their essential benefits in sensitivity, dynamic range, robustness, broad applicability, and suitability to automation. One approach has been to devise so-called homogeneous assay formats where no separation of an added detectably labeled specific binding partner is used. This type of methodology relies on devising a detection principle that is either turned on or turned off as a result of the binding reaction. In contrast, heterogeneous assays formats rely on physical separation of bound and free detectably labeled specific binding partners before quantitation.

Numerous U.S. patents have been issued in the field of homogeneous enzyme immunoassay. Many exploit the antibody:antigen binding reaction to either activate or inhibit a label enzyme: U.S. Pat. Nos. 3,817,837; 3,852,157; 3,875,011; 3,966,556; 3,905,871; 4,065,354; 4,043,872; 4,040,907; 4,039,385; 4,046,636; 4,067,774; 4,191,613; and 4,171,244, 4,785,080. Other homogeneous immunoassays involve various methods of quenching fluorescence through antibodies or other fluorescent quenchers: U.S. Pat. Nos. 3,998,943; 3,996,345; 4,174,384; 4,161,515; 4,208,479 and 4,160,016. Still other U.S. patents in this field of assorted types of immunoassay include: U.S. Pat. Nos. 3,935,074; 4,130,462; and 4,193,983. U.S. Pat. No. 4,160,645 discloses an assay method using an electron transfer catalyst as a label. The catalyst (label) is deactivated by bonding to antibody.

Campbell et al., (Biochem. J., 216, 185-194 (1983)), discloses a detection method using energy transfer between a chemiluminescence donor coupled to an antigen (Ag-L) and a fluorescence acceptor coupled to an antibody (Ab-F) in a competitive assay format. Complexed antigen ultimately emits at the wavelength of the fluorescer, while free antigen emits at the characteristic wavelength of the chemiluminescence label. Subsequently, the light intensity is measured at two wavelengths and the ratio of the two signals is related to the amount of analyte in the sample.

Various other homogeneous immunoassays are known: Rubenstein, et al, U.S. Pat. No. 3,817,837 (Homogeneous Enzyme Immunoassay), Ullman, U.S. Pat. No. 3,996,345 (Fluorescence Quenching Homogenous Immunoassay), Maggio, U.S. Pat. No. 4,233,402 (Enzyme Channeling Homogeneous Enzyme Immunoassay), and Boguslaski, et al, Canadian Patent 1,082,577 (Hapten-Cofactor Homogeneous Enzyme Immunoassay).

U.S. Pat. No. 6,406,913 to Ullman discloses assay methods comprising treating a medium suspected of containing an analyte under conditions such that the analyte causes a photosensitizer and a chemiluminescent compound to come into close proximity. The photosensitizer generates singlet oxygen, which diffuses through solution to and activates the chemiluminescent compound when it is in close proximity. The activated chemiluminescent compound subsequently produces light. The amount of light produced is related to the amount of analyte in the medium. In one embodiment, at least one of the photosensitizer and chemiluminescent compound is associated with a suspendible particle, and a specific binding pair member is bound thereto.

U.S. Pat. No. 5,516,636 to McCapra discloses assay methods comprising specific binding assays which utilize a sensitizer as a label. The sensitizer, when stimulated by radiation, electron transfer, electrolysis, electroluminescence or energy transfer, achieves an excited state, which (a) upon interaction with molecular oxygen produces singlet oxygen, or (b) upon interaction with a leucodye is reduced by oxygen to produce hydrogen peroxide. Either interaction with the excited sensitizer, with the addition of other reagents, produces a detectable signal.

Despite the considerable efforts made in devising homogeneous, or non-separation, assay formats, they still do not experience widespread commercial adoption. Heterogeneous assays are viewed as simpler to develop and mass-produce, albeit operationally more complex. In particular, the field of high volume clinical immunodiagnostics and the smaller field of clinical nucleic acid diagnostics are dominated by heterogeneous assay formats. Within this arena, test formats would be beneficial to the field that could simplify protocols, reduce complexity and improve compatibility with automation by removing unnecessary steps.

SUMMARY OF THE INVENTION

In one aspect, the present invention provides novel assay methods involving specific binding reactions, especially immunoassays, which are simplified compared to known methods. Assays are simplified by eliminating a separation and washing step prior to the detection step and thus are deemed non-separation assays. The methods feature the use of an immobilized chemiluminescent compound and an activator compound conjugated to a specific binding partner for inducing a chemiluminescent reaction. Analyte-mediated co-localization of the chemiluminescent label compound and the activator conjugate causes the ensuing chemiluminescent reaction to take place only at the site of the bound analyte molecules. The presence of unbound, excess activator conjugate does not contribute to or interfere with the chemiluminescent reaction. As a result, the intensity of chemiluminescence emitted is proportional to the quantity of analyte.

DETAILED DESCRIPTION OF THE INVENTION

Definitions

Figure 1:
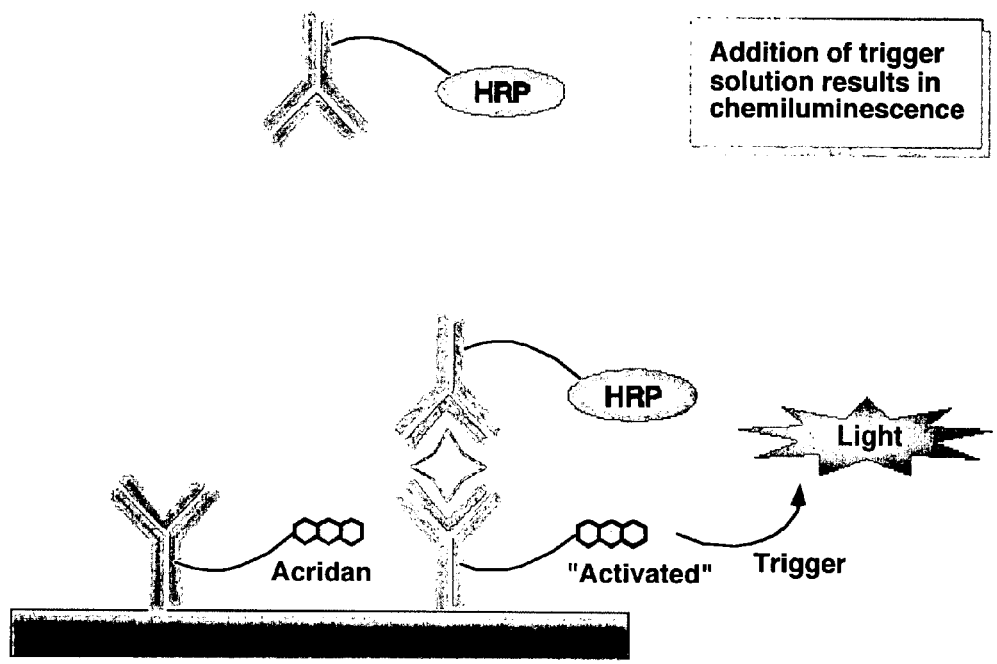
FIG. 1 is a schematic diagram of the detection step of an immunoassay conducted according to the invention using a labeled capture antibody.

Alkyl—A branched, straight chain or cyclic hydrocarbon group containing from 1-20 carbons which can be substituted with 1 or more substituents other than H. Lower alkyl as used herein refers to those alkyl groups containing up to 8 carbons.

Analyte—A substance in a sample to be detected in an assay. One or more substances having a specific binding affinity to the analyte will be used to detect the analyte. The analyte can be a protein, an antibody, or a hapten to which an antibody that binds it can be made. The analyte can be a nucleic acid which is bound by a complementary nucleic acid. The analyte can be any other substance which forms a member of a specific binding pair.

Aralkyl—An alkyl group substituted with an aryl group.

Aryl—An aromatic ring-containing group containing 1 to 5 carbocyclic aromatic rings, which can be substituted with 1 or more substituents other than H.

Biological material—includes whole blood, anticoagulated whole blood, plasma, serum, tissue, cells, cellular content, and viruses.

Chemiluminescent compound—A compound which undergoes a reaction resulting in it being converted into another compound formed in an electronically excited state. The excited state may be either a singlet or triplet excited state. The excited state may directly emit light upon relaxation to the ground state or may transfer excitation energy to an emissive energy acceptor, thereby returning to the ground state. The energy acceptor is raised to an excited state in the process and emits light.

Sample—A fluid containing or suspected of containing nucleic acids. Typical samples which can be used in the methods of the invention include bodily fluids such as blood, which can be anticoagulated blood as is commonly found in collected blood specimens, plasma, serum, urine, semen, saliva, cell cultures, tissue extracts and the like. Other types of samples include solvents, seawater, industrial water samples, food samples and environmental samples such as soil or water, plant materials, eukaryotes, bacteria, plasmids and viruses, fungi, and cells originated from prokaryotes.

Solid phase material—a material having a surface upon which assay components are immobilized. Materials can be in the form of particles, microparticles, nanoparticles, fibers, beads, membranes, filters and other supports such as test tubes and microwells.

Specific binding pair, specific binding partner—A molecule, including biological molecules having a specific binding affinity for another substance including DNA, RNA, oligonucleotides, antibodies, antibody fragments, antibody-DNA chimeras, antigens, haptens, proteins, lectins, avidin, streptavidin and biotin. Specific binding partners can be conjugated to one or more molecules of either an activator or a chemiluminescent compound.

Substituted—Refers to the replacement of at least one hydrogen atom on a group by a non-hydrogen group. It should be noted that in references to substituted groups it is intended that multiple points of substitution can be present unless clearly indicated otherwise.

The present invention is concerned with rapid and simple assay methods for detecting substances by means of specific binding pair reactions. The methods require the use of an immobilized chemiluminescent compound, an activator compound conjugated to a specific binding partner for inducing a chemiluminescent reaction, and a trigger solution. The methods involve one or more specific binding pair reactions for detecting the analyte. As a result of a labeled specific binding partner binding to the analyte, an activator is brought into proximity to an immobilized chemiluminescent compound so that it is effective to activate a reaction generating chemiluminescence upon addition of a trigger solution. The activator-labeled specific binding partner is provided to the system in excess to the amount needed to bind all of the analyte. The excess unbound activator conjugate is not removed prior to addition of triggers solution and detection since it can not participate in the reaction.

The present methods thus differ from conventional test methods in not requiring removal of the unbound activator conjugate present in great excess to the amount specifically associated with the analyte. Sample containing analyte, activator conjugate, and trigger solution can be added sequentially to a test vessel, without washing or separations, and the luminescence read. Alternately, sample and activator conjugate can be pre-mixed and added to the test vessel containing a specific binding partner for capturing the analyte and containing the immobilized chemiluminescent label before introducing the trigger solution. No washing or separation of excess unbound activator conjugate is required. Another point of difference with conventional chemiluminescent assays known in the art rests in the fact that neither the chemiluminescent compound nor the activator (e.g. peroxidase) that participates in light production is free to diffuse in solution. Both are spatially constrained. Partially as a consequence of this, signal generation tends to be of short duration.

Conventional assays using chemiluminescent substrates and enzyme labeled conjugates provide the substrate in great excess to the amount of label enzyme. Frequently, the molar ratio of substrate/enzyme can exceed nine powers of ten, i.e. a billion-fold excess. It is believed to be necessary to supply such an enormous excess of chemiluminescent compound in order to ensure an adequate supply of substrate for continuous enzymatic turnover and that this process guarantees adequate detection sensitivity in assay methods. Applicants have found that it is possible to devise highly sensitive assay methods that reduce this ratio by several orders of magnitude. In this regard these methods differ fundamentally from known methods.

Eliminating washing and separation steps as described above and as demonstrated in exemplary assays described below affords opportunities to simplify the design of assay protocols. The reduced number of operational steps decreases assay time, inter-assay variability from incomplete washing, and cost. At the same time it enhances the ability to automate and miniaturize assay performance with all of the inherent advantages attendant on automation and miniaturization.

Assays performed according to the present methods involve four steps. In a first step a solid phase is provided in a test device for specifically capturing an analyte of interest. The solid phase is provided with an immobilized specific binding partner for an analyte to be detected. The solid phase is further provided with chemiluminescent labeling compound immobilized thereon. The chemiluminescent label may be provided in a number of different ways as described in more detail below. In each variant the chemiluminescent label is irreversibly attached to a substance or material in a way that renders it immobile. In a second step the analyte-containing sample and the activator conjugate are introduced to the test device having the solid phase immobilized specific binding partner for the analyte and permitted to form specific binding complexes. The sample and activator conjugate can be added separately in either order, or simultaneously, or can be pre-mixed and added as a combination. An optional delay time to allow binding reactions to occur can be inserted at this point. In the third step a triggers solution is added to produce the chemiluminescence for detecting the analyte. Lastly the chemiluminescence is detected. Preferably either peak light intensity level or total integrated light intensity is measured. The quantity of light can be related to the amount of the analyte by constructing a calibration curve according to generally known methods. When light emission ensues rapidly after addition of trigger solution it is desirable to either mechanically time the onset of measurement to the addition by means of a suitable injector or to perform the addition with the test device already exposed to the detector.

Assay Formats and Solid Supports

Figure 2:
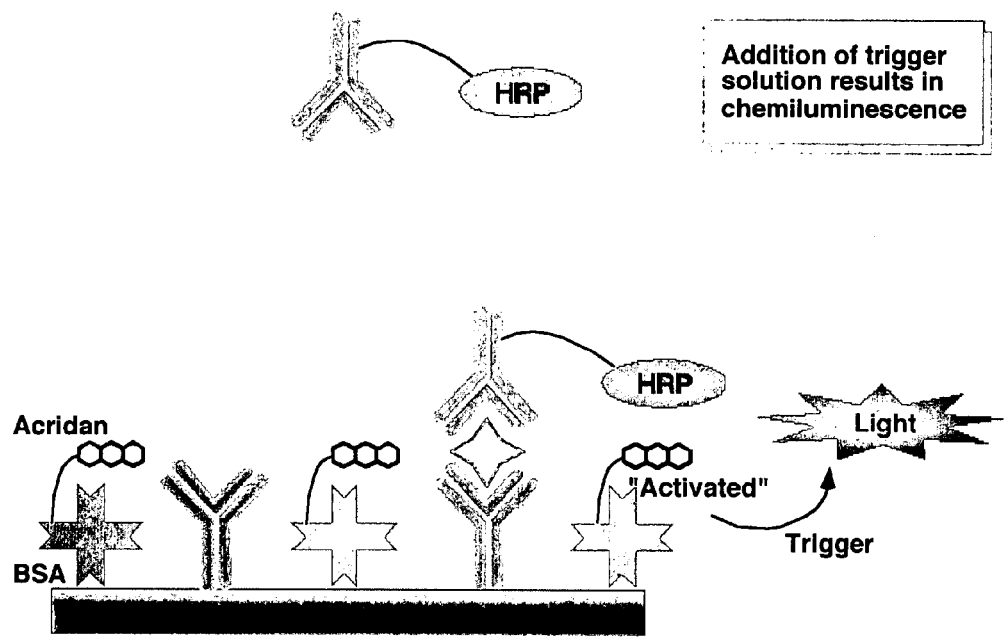
FIG. 2 is a schematic diagram of the detection step of another immunoassay conducted according to the invention using labeled blocking protein and an unlabeled capture antibody.
Figure 3:
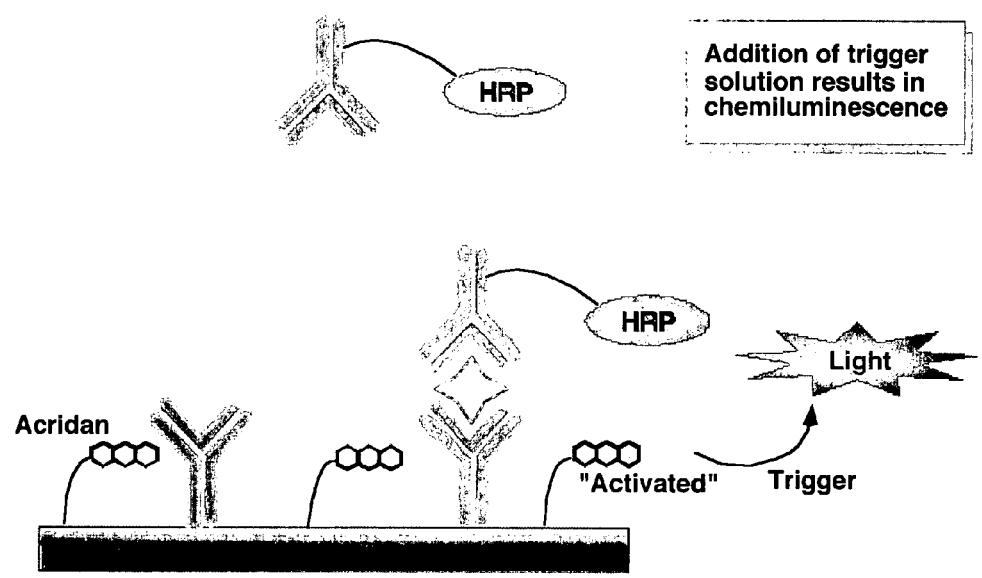
FIG. 3 is a schematic diagram of the detection step of another immunoassay conducted according to the invention using labeled solid surface and an unlabeled capture antibody.
Figure 4:
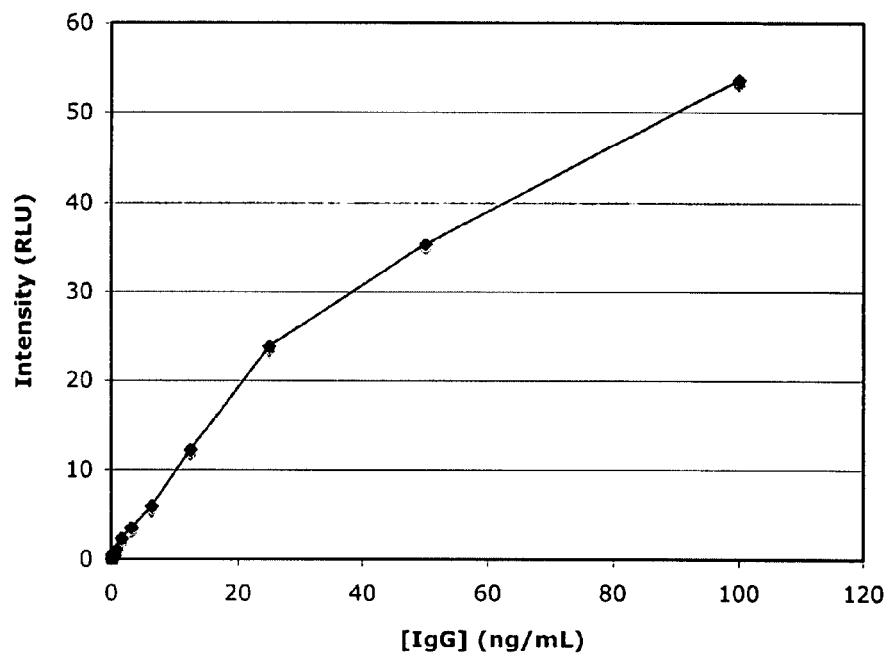
FIG. 4 is a graph showing detection of IgG antigen in a nonseparation immunoassay using a labeled capture antibody immobilized in the wells of a microplate and excess anti-IgG-HRP conjugate for detection.
Figure 5:
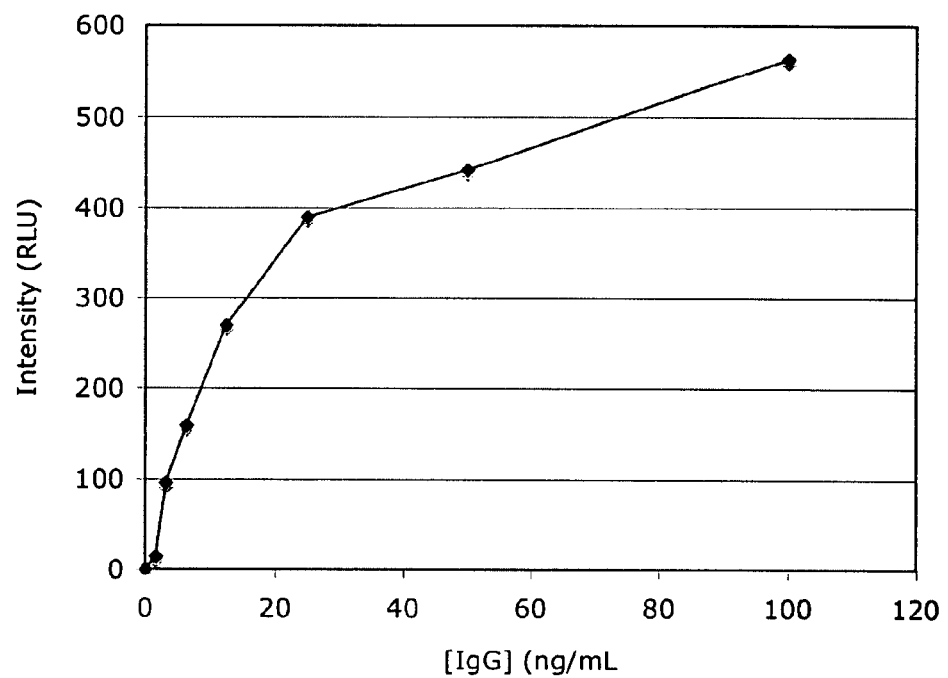
FIG. 5 is a is a graph showing detection of IgG antigen in a nonseparation immunoassay using labeled blocking protein and an unlabeled capture antibody immobilized in the wells of a microplate and excess anti-IgG-HRP conjugate for detection.

In the methods of the present invention, the chemiluminescent labeling compound is immobilized to a component of the test system. This can be accomplished in any of several ways. In one embodiment the chemiluminescent label is covalently linked to an immobilized specific binding partner for the analyte. An example would be a capture antibody immobilized on the wells of a microplate. Immobilization of the specific binding partner can be by covalent linkage or by an adsorption process. In this format, depicted in FIG. 1, the chemiluminescent label becomes associated with the activator by virtue of two specific binding partners both binding an analyte in a "sandwich" format. In another embodiment, depicted in FIG. 2, the chemiluminescent label is covalently linked to an auxiliary substance that is immobilized on the solid support in a random manner. Immobilization of the auxiliary substance can be by covalent linkage or by an adsorption process. The label is thereby distributed more or less uniformly about the surface of the solid support. A means is provided for attracting the analyte to the surface, e.g. by an unlabeled specific binding partner for the analyte. The chemiluminescent label becomes associated with the activator by virtue of a specific binding reaction bringing the activator near the chemiluminescent label attached to the auxiliary substance passively coated onto the surface of the support. In another embodiment, the chemiluminescent label is covalently linked to the surface of the solid support. As depicted in FIG. 3, the label is thereby distributed more or less uniformly about the surface of the solid support. A means is provided for attracting the analyte to the surface, e.g. by an unlabeled specific binding partner for the analyte. The chemiluminescent label becomes associated with the activator by virtue of a specific binding reaction bringing the activator near the chemiluminescent label directly attached to the surface of the support. Then, without washing or separation, the trigger solution is added and chemiluminescence measured.

Figure 7:
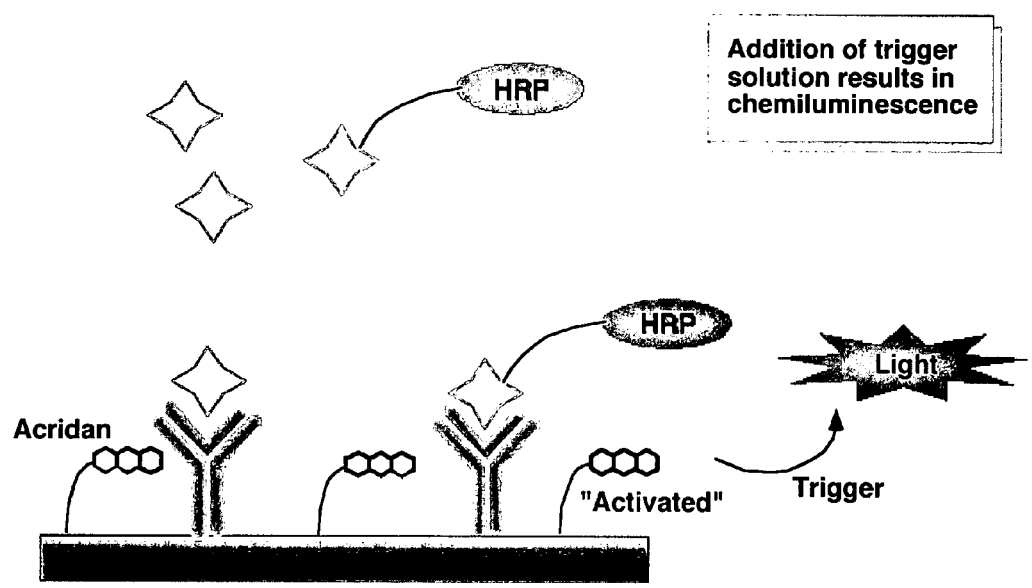
FIG. 7 is a schematic diagram of the detection step of a competitive immunoassay conducted according to the invention using a labeled solid phase, an immobilized capture antibody and a labeled analyte analog.

Another embodiment comprises a variation wherein an analog of the analyte is used comprising an activator-analyte conjugate. The analyte analog and analyte will competitively bind with the specific binding partner for the analyte. It will be apparent that in this type of assay method a negative correlation between the amount of analyte in the sample and the intensity of chemiluminescence will result. (FIG. 7)

Figure 6:
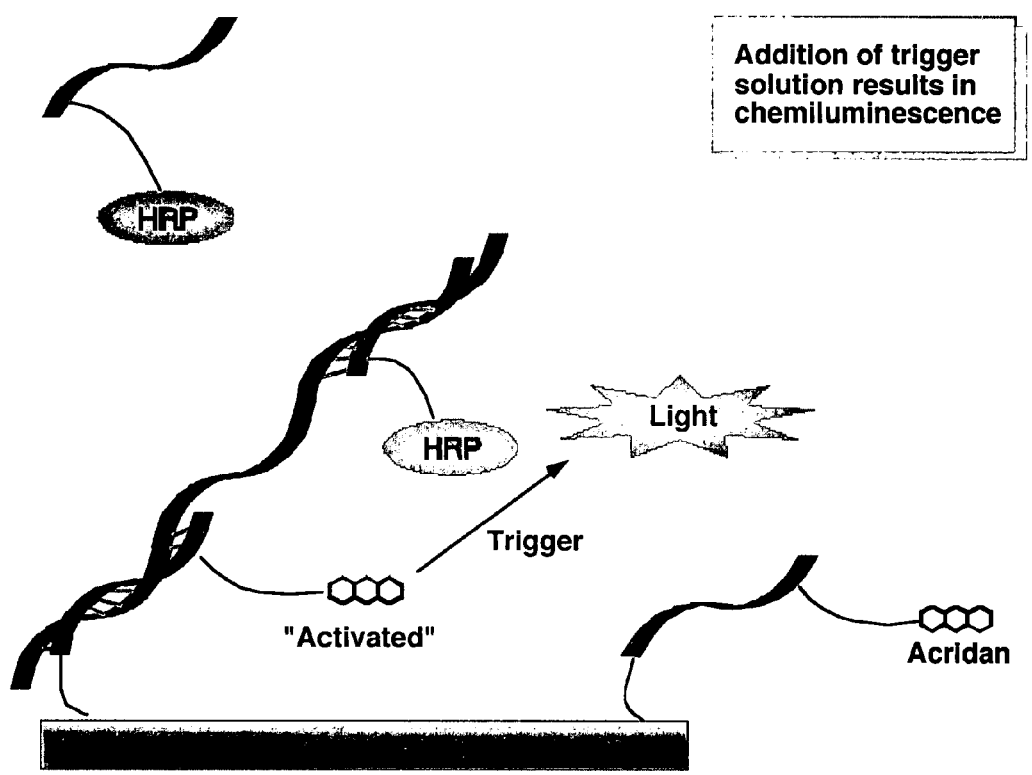
FIG. 6 is a schematic diagram of the detection step of a nucleic acid hybridization assay conducted according to the invention using a labeled capture nucleic acid.

In addition to attachment of chemiluminescent label through antibodies for binding antigens or other proteins or other antibodies via an immunoassay, the present methods can use chemiluminescent-labeled nucleic acids for detecting nucleic acids through binding of complementary nucleic acids. The use in this regard is not particularly limited with regard to the size of the nucleic acid, the only criterion being that the complementary partners be of sufficient length to permit stable hybridization. Nucleic acids as used herein includes gene length nucleic acids, shorter fragments of nucleic acids, polynucleotides and oligonucleotides, any of which can be single or double stranded. In the practice of the invention using nucleic acids as specific binding partners, a nucleic acid is covalently attached or physically immobilized on a surface of a solid support to capture an analyte nucleic acid. The chemiluminescent label can be attached to the capture nucleic acid, as shown schematically in FIG. 6, or the label can be associated with the solid phase directly as explained above. The capture nucleic acid will have full or substantially full sequence complementarity to a sequence region of the analyte nucleic acid. When substantially complementary, the capture nucleic acid may possess a terminal overhanging portion, a terminal loop portion or an internal loop portion that is not complementary to the analyte provided that it does not interfere with or prevent hybridization with the analyte. The reverse situation may also occur where the overhang or loop resides within the analyte nucleic acid. Capture nucleic acid, analyte nucleic acid and an conjugate of an activator and a third nucleic acid are allowed to hybridize. The third nucleic acid is substantially complementary to a sequence region of the analyte nucleic acid different from the region complementary to the capture nucleic acid. The hybridization of the capture nucleic acid and activator conjugate nucleic acid with the analyte can be performed consecutively in either order or simultaneously. As a result of this process, the chemiluminescent label becomes associated with the activator by virtue of specific hybridization reactions bringing the activator near the chemiluminescent label directly attached to the surface of the support. Trigger solution is provided and chemiluminescence detected as described above.

Another embodiment comprises a variation wherein a conjugate of the analyte with the activator is used. The analyte nucleic acid-activator conjugate and analyte nucleic acid will competitively bind with the specific binding partner for the analyte nucleic acid. It will be apparent that in this type of assay method a negative correlation between the amount of analyte in the sample and the intensity of chemiluminescence will result.

In addition to antibody-based and nucleic acid-based systems, other specific binding pairs as are generally known to one of ordinary skill in the art of binding assays can serve as the basis for test methods according to the present invention. The fluorescein/anti-fluorescein, digoxigenin/anti-digoxigenin, and nitrophenyl/anti-nitrophenyl pairs are exemplary. As a further example, the well known (strept)avidin/biotin binding pair can be utilized. To illustrate one way in which this binding pair could be used a streptavidin-chemiluminescent label conjugate can be covalently linked or adsorbed onto a solid support. A biotin-labeled analyte and an activator conjugate is then added, wherein the conjugate is attached to an anti-biotin antibody or anti-analyte antibody. After complexes are allowed to form the trigger solution is added and detection conducted as above. These and other examples that will occur to one of skill in the art are considered to be within the scope of the present inventive methods.

Solid supports useful in the practice of the present invention can be of various materials, shapes, and sizes. Materials already in use in binding assays including microwell plates of the 96-well, 384-well or higher number varieties, test tubes, sample cups, plastic spheres, cellulose, paper or plastic test strips, latex particles, polymer particles, silica particles, magnetic particles, especially those having average diameters of 0.1-10 μm, and nanoparticles of various materials can all provide a useful solid support for attachment of chemiluminescent labels and for immobilizing specific binding partners. The present disclosure teaches methods of functionalizing such materials for use in the present assay methods. In particular, methods are disclosed for attaching both a chemiluminescent labeling compounds and a specific binding partner, such as an antibody, to the same surface, especially to a microparticle.

Chemiluminescent Label Compounds

The compounds used as chemiluminescent labels in the practice of the present invention have the general formula CL-L-RG wherein CL denotes a chemiluminescent moiety, L denotes a linking moiety to link the chemiluminescent moiety and a reactive group, and RG denotes a reactive group moiety for coupling to another material. The chemiluminescent moiety CL comprises. It is desirable, but not necessary, that the chemiluminescent reaction of the CL group, the activator and the trigger solution be rapid, desirably taking place over a very brief time span.

Preferred chemiluminescent compounds are capable of being oxidized to produce chemiluminescence in the presence of the activator and a trigger solution. An exemplary class of compounds which by incorporation of a linker and reactive group could serve as the chemiluminescent label include luminol, and structurally related cyclic hydrazides including isoluminol, aminobutylethylisoluminol (ABEI), aminohexylethylisoluminol (AHEI), 7-dimethylaminonaphthalene-1,2-dicarboxylic acid hydrazide, ring-substituted aminophthalhydrazides, anthracene-2,3-dicarboxylic acid hydrazides, phenathrene-1,2-dicarboxylic acid hydrazides, pyrenedicarboxylic acid hydrazides, 5-hydroxy-phthalhydrazide, 6-hydroxyphthalhydrazide, as well as other phthalazinedione analogs disclosed in U.S. Pat. No. 5,420,275 to Masuya et al. and in U.S. Pat. No. 5,324,835 to Yamaguchi.

Another class of chemiluminescent moieties include acridan esters, thioesters and sulfonamides disclosed in U.S. Pat. Nos. 5,491,072, 5,523,212, 5,593,845, and 6,030,803.

Another class of chemiluminescent moieties includes the heterocyclic compounds disclosed in U.S. Pat. No. 5,922,558; 6,696,569; and 6,891,057. These compounds preferably comprise a heterocyclic ring, preferably comprising a nitrogen, oxygen or sulfur-containing five or six-membered ring or multiple ring group to which is bonded an exocyclic double bond, the terminal carbon of which is substituted with two atoms selected from oxygen, and sulfur atoms.

It is considered that any compound known to produce chemiluminescence by the action of hydrogen peroxide and a peroxidase will function as the chemiluminescent moiety of the chemiluminescent label compound used in the present invention. Numerous such compounds of various structural classes, including xanthene dyes, aromatic amines and heterocyclic amines are known in the art to produce chemiluminescence under these conditions.

A preferred group of chemiluminescent label compounds useful in the methods of the invention comprises acridan compounds having formula I

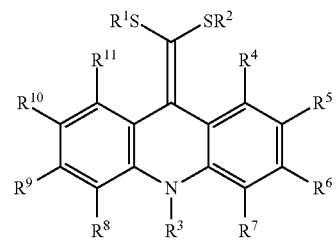

wherein at least one of the groups $R^1$-$R^{11}$ is a labeling substituent of the formula

-L-RG wherein L is a linking group which can be a bond or another divalent or polyvalent group, RG is a reactive group which enables the chemiluminescent labeling compound to be bound to another compound, $R^1$, $R^2$ and $R^3$ are organic groups containing from 1 to 50 non-hydrogen atoms, and each of $R^4$-$R^{11}$ is hydrogen or a noninterfering substituent. The labeling substituent -L-RG is present preferably on one of $R^1$ or $R^2$ although it can also be present as a substituent on $R^3$ or one of $R^4$-$R^{11}$.

The groups $R^1$ and $R^2$ in the compound of formula I can be any organic group containing from 1 to about 50 non hydrogen atoms selected from C, N, O, S, P, Si and halogen atoms which allows light production. By the latter is meant that when a compound of formula I undergoes a reaction of the present invention, an excited state product compound is produced and can involve the production of one or more chemiluminescent intermediates. The excited state product can emit the light directly or can transfer the excitation energy to a fluorescent acceptor through energy transfer causing light to be emitted from the fluorescent acceptor. $R^1$ and $R^2$ are preferably selected from substituted or unsubstituted alkyl, substituted or unsubstituted alkenyl, substituted or unsubstituted alkynyl, substituted or unsubstituted aryl, substituted or unsubstituted aralkyl groups of 1-20 carbon atoms. When $R^1$ or $R^2$ is a substituted group, it is substituted with 1-3 atoms or groups selected from carbonyl groups, carboxyl groups, tri(C1-C8 alkyl)silyl groups, an SO3-group, an OSO3-2 group, glycosyl groups, a PO3-group, an OPO3-2 group, halogen atoms, a hydroxyl group, a thiol group, amino groups, quaternary ammonium groups, quaternary phosphonium groups. In a preferred embodiment, $R^1$ or $R^2$ is preferably substituted with the labeling substituent of the formula -L-RG where L is a linking group and RG is a reactive group.

The group $R^3$ is an organic group containing from 1 to 50 atoms non-hydrogen atoms selected from C, N, O, S, P, Si and halogen atoms in addition to the necessary number of H atoms required satisfy the valences of the atoms in the group. More preferably $R^3$ contains from 1 to 20 non-hydrogen atoms. The organic group is preferably selected from the group consisting of alkyl, substituted alkyl, substituted or unsubstituted alkenyl, substituted or unsubstituted alkynyl, substituted or unsubstituted aryl, substituted or unsubstituted aralkyl groups of 1-20 carbon atoms. More preferred groups for R3 include substituted or unsubstituted $C_1$-$C_4$ alkyl groups, phenyl, substituted or unsubstituted benzyl groups, alkoxyalkyl, carboxyalkyl and alkylsulfonic acid groups. The group $R^3$ can be joined to either $R^7$ or $R^8$ to complete a 5 or 6-membered ring. In one embodiment, $R^3$ is substituted with the labeling substituent of the formula -L RG.

In the compounds of formula I, the groups $R^4$-$R^{11}$ each are independently H or a substituent group which permits the excited state product to be produced and generally contain from 1 to 50 atoms selected from C, N, O, S, P, Si and halogen atoms. Representative substituent groups which can be present include, without limitation, alkyl, substituted alkyl, aryl, substituted aryl, aralkyl, alkenyl, alkynyl, alkoxy, aryloxy, halogen, amino, substituted amino, carboxyl, carboalkoxy, carboxamide, cyano, and sulfonate groups. Pairs of adjacent groups, e.g. $R^4$-$R^5$ or $R^5$-$R^6$, can be joined together to form a carbocyclic or heterocyclic ring system comprising at least one 5 or 6-membered ring which is fused to the ring to which the two groups are attached. Such fused heterocyclic rings can contain N, O or S atoms and can contain ring substituents other than H such as those mentioned above. One or more of the groups $R^4$-$R^{11}$ can be a labeling substituent of the formula -L-RG. It is preferred that $R^4$-$R^{11}$ are selected from hydrogen, halogen and alkoxy groups such as methoxy, ethoxy, t-butoxy and the like. A preferred group of compounds has one of $R^5$, $R^6$, $R^9$ or $R^{10}$ as a halogen and the other of $R^4$-$R^{11}$ are hydrogen atoms.

Substituent groups can be incorporated in various quantities and at selected ring or chain positions in the acridan ring in order to modify the properties of the compound or to provide for convenience of synthesis. Such properties include, e.g. chemiluminescence quantum yield, rate of reaction with the enzyme, maximum light intensity, duration of light emission, wavelength of light emission and solubility in the reaction medium. Specific substituents and their effects are illustrated in the specific examples below, which, however, are not to be considered limiting the scope of the invention in any way. For synthetic expediency compounds of formula I desirably have each of $R^4$ to $R^{11}$ as a hydrogen atom.

Linking group (L). The linking group can be a bond, an atom, divalent groups and polyvalent groups, or a straight, or branched chain of atoms some of which can be part of a ring structure. The substituent usually contains from 1 to about 50 non-hydrogen atoms, more usually from 1 to about 30 non-hydrogen atoms. Atoms comprising the chain are selected from C, O, N, S, P, Si, B, and Se atoms, preferably from C, O, N, P and S atoms. Halogen atoms can be present as substituents on the chain or ring. Typical functional groups comprising the linking substituent include alkylene, arylene, alkenylene, ether, peroxide, carbonyl as a ketone, ester, carbonate ester, thioester, or amide group, amine, amidine, carbamate, urea, imine, imide, imidate, carbodiimide, hydrazine, diazo, phosphodiester, phosphotriester, phosphonate ester, thioether, disulfide, sulfoxide, sulfone, sulfonate ester, sulfate ester, and thiourea groups.

Reactive group. The reactive group RG is an atom or group whose presence facilitates bonding to another molecule by covalent attachment or physical forces. In some embodiments, attachment of a chemiluminescent labeling compound of the present invention to another compound will involve loss of one or more atoms from the reactive group for example when the reactive group is a leaving group such as a halogen atom or a tosylate group and the chemiluminescent labeling compound is covalently attached to another compound by a nucleophilic displacement reaction. In other embodiments, attachment of a chemiluminescent labeling compound to another compound by covalent bond formation will involve reorganization of bonds within the reactive group as occurs in an addition reaction such as a Michael addition or when the reactive group is an isocyanate or isothiocyanate group. In still other embodiments, attachment will not involve covalent bond formation, but rather physical forces in which case the reactive group remains unaltered. By physical forces is meant attractive forces such as hydrogen bonding, electrostatic or ionic attraction, hydrophobic attraction such as base stacking, and specific affinity interactions such as biotin-streptavidin, antigen-antibody and nucleotide-nucleotide interactions.

Table 1. Reactive Groups for Chemical Binding of Labels to Organic and Biological Molecules a.) Amine Reactive Groups.

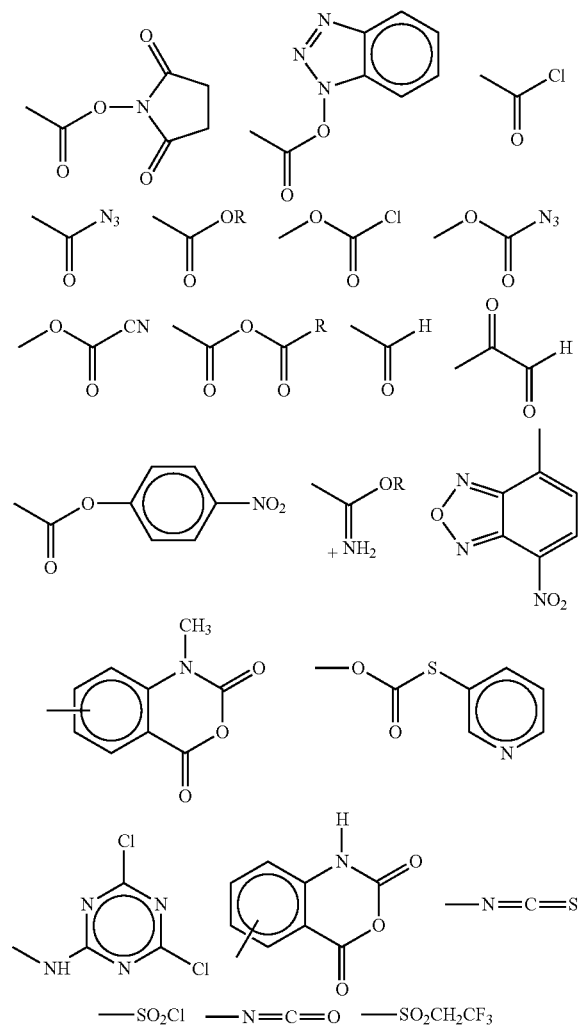

b.) Thiol Reactive Groups.

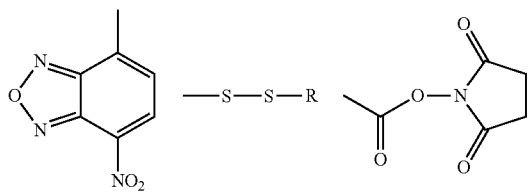

X = Cl, Br, I

3) Carboxylic Acid Reactive Groups.

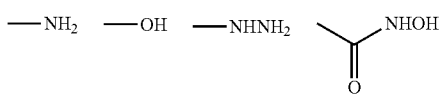

4) Hydroxyl Reactive Groups.

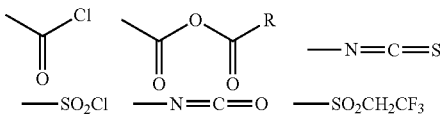

5) Aldehyde/Ketone Reactive Groups.

—NH$_2$—ONH$_2$—NHNH$_2$

6) Other Reactive Group Pairs.

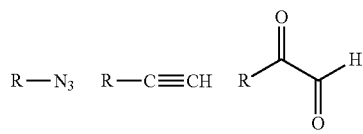

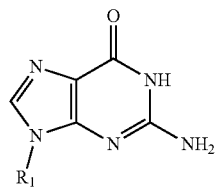

Preferred reactive groups include OH, NH$_2$, ONH$_2$, NHNH$_2$, COOH, SO$_2$CH$_2$CF$_3$, N-hydroxysuccinimide ester, N-hydroxysuccinimide ether and maleimide groups.

Bifunctional coupling reagents can also be used to couple labels to organic and biological molecules with moderately reactive groups (see L. J. Kricka, *Ligand-Binder Assays*, Marcel Dekker, Inc., New York, 1985, pp. 18-20, Table 2.2 and T. H Ji, "Bifunctional Reagents," *Methods in Enzymology*, 91, 580-609 (1983)). There are two types of bifunctional reagents: those that become incorporated into the final structure, and those that do not and serve only to couple the two reactants.

A preferred group of compounds have formula II wherein each of $R^4$ to $R^{11}$ are hydrogen. The groups $R^1$, $R^2$ and $R^3$ are as defined above.

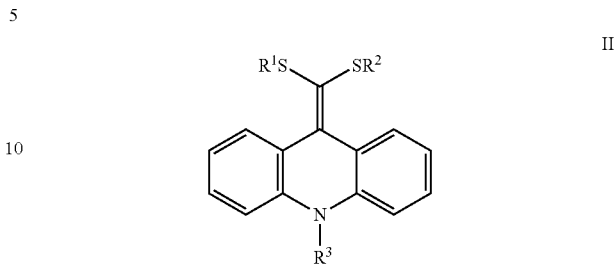

Preferred labeling compounds have of formulas I have the groups -L-RG as a substituent on the group $R^1$ or $R^2$. A preferred labeling compound has formula III.

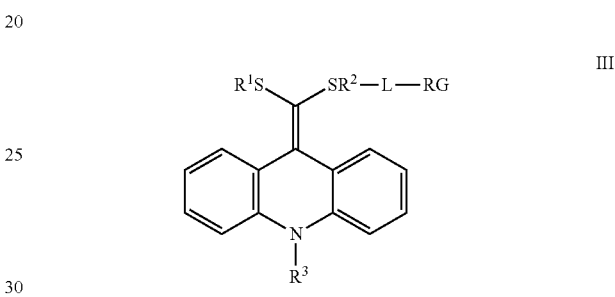

Representative preferred labeling compounds and their use in attachment to other molecules and solid surfaces is described in the specific examples below.

Activator Conjugate

The activator compound forms part of an activator-specific binding partner conjugate. The conjugate serves a dual function; 1) binding specifically to the analyte in the assay through the specific binding partner portion, either directly or through an intermediary specific binding partner, and 2) activating the chemiluminescent compound through the activator portion. The activator portion of the conjugate is a compound that effects the activation of the chemiluminescent compound so that, in the presence of the trigger solution, chemiluminescence is produced. Compounds capable of serving as the activator include transition metal salts and complexes and enzymes, especially transition metal-containing enzymes, most especially peroxidase enzymes. Transition metals useful in activator compounds include those of groups 3-12 of the periodic table, especially iron, copper, cobalt, zinc, manganese, and chromium. It should be noted that the activator molecules responsible for signal generation may operate within a physically confined radius and only have contact with a finite supply of chemiluminescent compound. This would seem to preclude large catalytic turnover in cases where the activator possesses that potential.

The peroxidase which can undergo the chemiluminescent reaction include lactoperoxidase, microperoxidase, myeloperoxidase, haloperoxidase, e.g. vanadium bromoperoxidase, horseradish peroxidase, fungal peroxidases such as lignin peroxidase and peroxidase from Arthromyces ramosus and Mn-dependent peroxidase produced in white rot fungi, and soybean peroxidase. Other peroxidase mimetic compounds which are not enzymes but possess peroxidase-like activity including iron complexes, such as heme, and Mn-TPPS$_4$ (Y.-X. Ci, et al., Mikrochem. J., 52, 257-62 (1995)) are known which catalyze the chemiluminescent oxidation of substrates are explicitly considered to be within the scope of the meaning of peroxidase as used herein.

Conjugates or complexes of a peroxidase and a biological molecule can also be used in the method for producing chemiluminescence, the only proviso being that the conjugate display peroxidase activity. Biological molecules which can be conjugated to one or more molecules of a peroxidase include DNA, RNA, oligonucleotides, antibodies, antibody fragments, antibody-DNA chimeras, antigens, haptens, proteins, lectins, avidin, streptavidin and biotin. Complexes including or incorporating a peroxidase, such as liposomes, micelles, vesicles and polymers which are functionalized for attachment to biological molecules, can also be used in the methods of the present invention.

Trigger Solution

The trigger solution provides a reactant necessary for generating the excited state compound necessary for chemiluminescence. The reactant may be one necessary for performing the chemiluminescent reaction by reacting directly with the chemiluminescent label. It may serve instead of or in addition to this function to facilitate the action of the activator compound. This will be the case, for example, when the activator is a peroxidase enzyme. In a preferred embodiment the trigger solution comprises a peroxide compound. The peroxide component is any peroxide or alkyl hydroperoxide capable of reacting with the peroxidase. Preferred peroxides include hydrogen peroxide, urea peroxide, and perborate salts. A representative embodiment uses a peroxidase conjugate as the activator, an acridan labeled of an analyte wherein the acridan label is provided by reacting the specific binding partner with a compound of formula III above, and a trigger solution comprising hydrogen peroxide. The peroxide reacts with the peroxidase, presumably to change the oxidation state of the iron in the active site of the enzyme to a different oxidation state. This altered state of the enzyme reacts with the acridan label maintained in proximity to the enzyme. The chemiluminescent reaction comprises a further reaction of an intermediate formed from the chemiluminescent compound with peroxide to produce the ultimate reaction product and light.

Incorporation of certain enhancer compounds into the trigger solution promotes the reactivity of the enzyme. Included among these enhancers are phenolic compounds and aromatic amines known to enhance other peroxidase reactions as described in U.S. Pat. Nos. 5,171,668 and 5,206,149, which are incorporated herein by reference. Substituted and unsubstituted arylboronic acid compounds and their ester and anhydride derivatives as disclosed in U.S. Pat. No. 5,512,451 and incorporated herein by reference are also considered to be within the scope of enhancers useful in the present invention. Preferred enhancers include but are not limited to: p-phenylphenol, p-iodophenol, p-bromophenol, p-hydroxycinnamic acid, p-imidazolylphenol, acetaminophen, 2,4-dichlorophenol, 2-naphthol and 6-bromo-2-naphthol. Mixtures of more than one enhancer from those classes mentioned above can also be employed.

Additional enhancers found to be effective in enhancing the production of chemiluminescence from compounds of the present invention are derivatives of phenoxazine and phenothiazine having the formulas below.

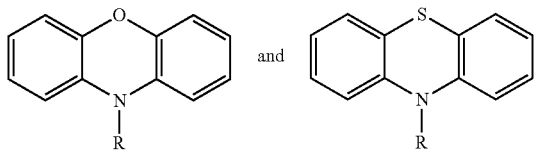

R groups substituted on the nitrogen atom of phenoxazine and phenothiazine enhancers include alkyl of 1-8 carbon atoms, and alkyl of 1-8 carbon atoms substituted with a sulfonate salt or carboxylate salt group. Preferred enhancers include 3-(N-phenothiazinyl)-propanesulfonic acid salts, 3-(N-phenoxazinyl)propanesulfonic acid salts, 4-(N-phenoxazinyl)butanesulfonic acid salts, 5-(N-phenoxazinyl)-pentanoic acid salts and N-methylphenoxazine and related homologs.

The detection reaction of the present invention is performed with a trigger solution which is typically in an aqueous buffer. Suitable buffers include any of the commonly used buffers capable of maintaining an environment permitting the chemiluminescent reaction to proceed. Typically the trigger solution will have a pH in the range of about 5 to about 10.5. Exemplary buffers include phosphate, borate, acetate, carbonate, tris(hydroxy-methylamino)methane [tris], glycine, tricine, 2-amino-2-methyl-1-propanol, diethanolamine MOPS, HEPES, MES and the like.

The trigger solution can also contain one or more detergents or polymeric surfactants to enhance the luminescence efficiency of the light-producing reaction or improve the signal/noise ratio of the assay. Nonionic surfactants useful in the practice of the present invention include by way of example polyoxyethylenated alkylphenols, polyoxyethylenated alcohols, polyoxyethylenated ethers and polyoxyethylenated sorbitol esters. Monomeric cationic surfactants, including quaternary ammonium salt compounds such as CTAB and quaternary phosphonium salt compounds can be used. Polymeric cationic surfactants including those comprising quaternary ammonium and phosphonium salt groups can also be used for this purpose.

Light emitted by the present method can be detected by any suitable known means such as a luminometer, x-ray film, high speed photographic film, a CCD camera, a scintillation counter, a chemical actinometer or visually. Each detection means has a different spectral sensitivity. The human eye is optimally sensitive to green light, CCD cameras display maximum sensitivity to red light, X-ray films with maximum response to either UV to blue light or green light are available. Choice of the detection device will be governed by the application and considerations of cost, convenience, and whether creation of a permanent record is required. In those embodiments where the time course of light emission is rapid, it is advantageous to perform the triggering reaction to produce the chemiluminescence in the presence of the detection device. As an example the detection reaction may be performed in a test tube or microwell plate housed in a luminometer or placed in front of a CCD camera in a housing adapted to receive test tubes or microwell plates.

Uses

The present assay methods find applicability in many types of specific binding pair assays. Foremost among these are chemiluminescent enzyme linked immunoassays, such as an ELISA. Various assay formats and the protocols for performing the immunochemical steps are well known in the art and include both competitive assays and sandwich assays. Types of substances that can be assayed by immunoassay according to the present invention include proteins, antibodies, haptens, drugs, steroids and other substances that are generally known in the art of immunoassay.

The methods of the present invention are also useful for the detection of nucleic acids by the use of enzyme-labeled nucleic acid probes. Exemplary methods include solution hybridization assays, DNA detection in Southern blotting, RNA by Northern blotting, DNA sequencing, DNA fingerprinting, colony hybridizations and plaque lifts, the conduct of which is well known to those of skill in the art.

In addition to the aforementioned antigen-antibody, hapten-antibody or antibody-antibody pairs, specific binding pairs also can include complementary oligonucleotides or polynucleotides, avidin-biotin, streptavidin-biotin, hormone-receptor, lectin-carbohydrate, IgG protein A, nucleic acid-nucleic acid binding protein and nucleic acid-anti-nucleic acid antibody. Receptor assays used in screening drug candidates are another area of use for the present methods. Any of these binding pairs can be adapted to use in the present methods by the three-component sandwich technique or the two-component competitive technique described above.

The present invention also contemplates providing kits for performing assays in accordance with the methods of the present invention. Kits may comprise, in packaged combination, chemiluminescent labels as either the free labeling compounds, chemiluminescent labeled specific binding partners, chemiluminescent derivatized solid supports, such as particles or microplates, or chemiluminescent labeled auxiliary substances such as blocking proteins, along with a trigger solution and instructions for use. Kits may optionally also contain activator conjugates, analyte calibrators, diluents and reaction buffers if chemiluminescent labeling is to be performed by the user.

EXAMPLES

Example 1

Synthesis of Compound 1

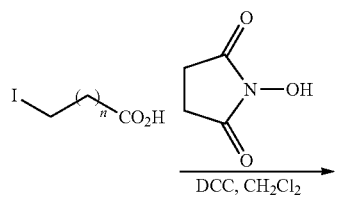

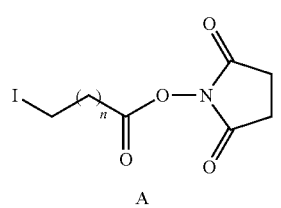

A

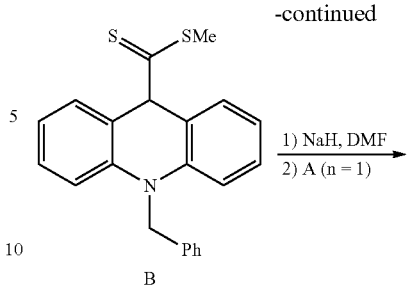

B

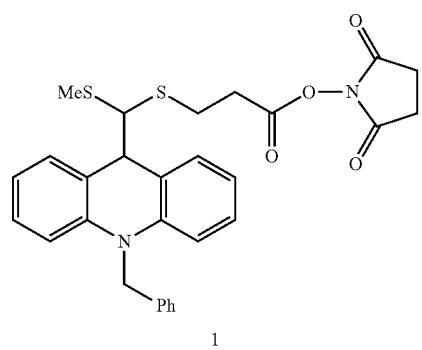

1

The iodocarboxylate NHS ester was synthesized by reacting the iodocarboxylic acids with N-hydroxy succinimide using DCC as the coupling reagent.

To a solution of dithioester B (1.808 g, 5.00 mmol) in anhydrous DMF (50 mL) was added NaH (60% in mineral oil, 0.200 g, 5.00 mmol) under argon. After 4 h at room temperature NHS 3-iodopropionate A (1.485 g, 5.00 mmol) was added and the resulting mixture was stirred overnight. DMF was removed in vacuo. Column chromatography with $CH_2Cl_2$/EtOAc (40:1) afforded 1.770 g of 1 as a yellow solid (yield 67%). $^1$H NMR (300 MHz, CDCl3): δ 2.30 (s, 3H), 2.74 (t, 2H), 2.83 (s, 4H), 3.01 (t, 2H), 5.31 (s, 2H), 6.88(t, 2H), 7.07 (m, 2H), 7.11-7.18 (m, 3H), 7.27 (m, 4H), 7.82 (dd, 1H), 7.89 (dd, 1H) ppm.

Example 2

Synthesis of Compound 2

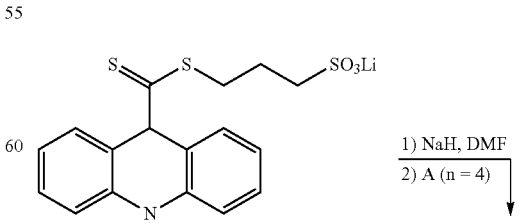

C

-continued

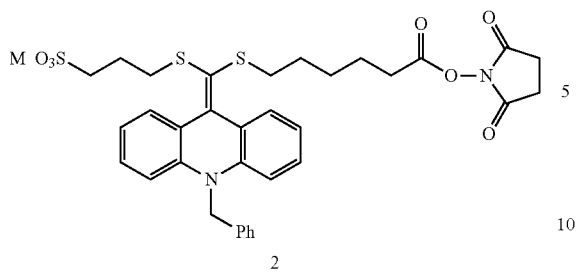

2

A mixture of dithioester C (0.692 g, 1.50 mmol) and NaH (60% in mineral oil, 0.060 g, 1.50 mmol) in anhydrous DMF (20 mL) was stirred under argon at room temperature for 4 hours, resulting a slightly cloudy solution. NHS 6 iodohexanoate A (0.661 g, 1.95 mmol) was then added in DMF (5 mL). After 16 h, DMF was removed in vacuo. To the residue was added 10 mL of acetone followed by 20 mL of ether. The supernatant was decanted. The precipitate was washed three times following the same procedures. After drying under vacuum, 1.200 g of 2 was obtained as a yellow solid. $^1$H NMR (300 MHz, CD$_3$OD): δ 1.15 (m, 2H), 1.33-1.47 (m, 4H), 2.01 (p, 2H), 2.38 (t, 2H), 2.67 (t, 2H), 2.75 (t, 2H), 2.82 (s, 4H), 2.88 (t, 2H), 5.32 (s, 2H), 6.88 6.93 (m, 2H), 7.00 (t, 2H), 7.08-7.28 (m, 7H), 7.83 (d, 1H), 7.92 (d, 1H) ppm.

Example 3

Synthesis of Compounds 3 and 4

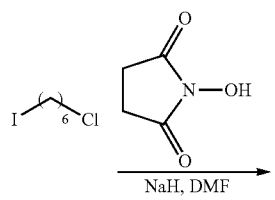

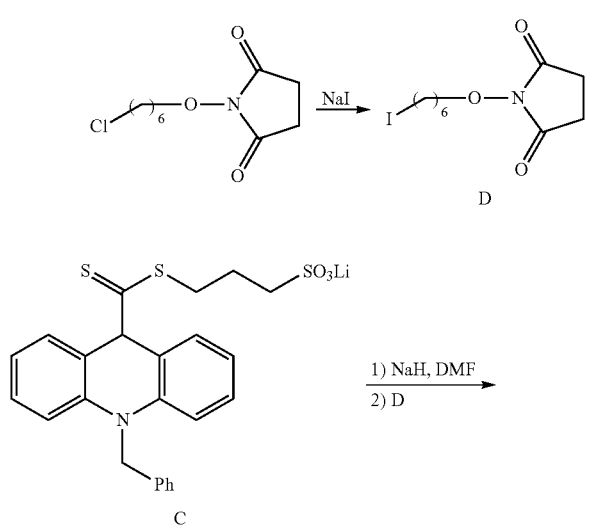

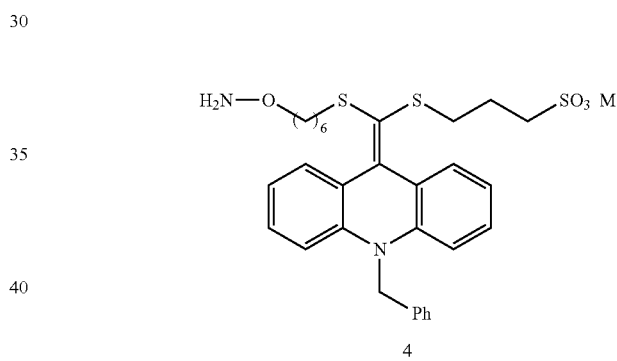

A mixture of dithioester C (1.00 g, 2.10 mmol) and NaH (60% in mineral oil, 0.087 g, 2.16 mmol) in anhydrous DMF (20 mL) was stirred under argon at room temperature for 4 hours, resulting in a slightly cloudy solution. N-6 iodohexoxysuccinimide D (0.82 g, 2.52 mmol) was then added in DMF (5 mL). The mixture was stirred over night after which DMF was removed in vacuo. The residue was washed four times with 30 mL of ether giving 1.35 g of 3.

Compound 3 (0.25 g) was dissolved in 5 mL of methanol to which was added 5.0 mL of 50% aq. NH2OH. After stirring the solution for 2 days, the solvents were evaporated under vacuum. The residue was washed with 6×20 mL of ether giving 0.21 g of 4. $^1$H NMR (300 MHz, CD$_3$OD): δ 1.14 (m, 4H), 1.40 (m, 4H), 1.94 (p, 2H), 2.65-2.71 (m, 4H), 2.84 (t, 2H), 3.55 (t, 2H), 5.31 (s, 2H), 6.88 (d, 2H), 6.98 (q, 2H), 7.10 (m, 4H), 7.12-7.27 (m, 3H), 7.85 (t, 2H) ppm.

Example 4

Synthesis of Compounds 5 and 6

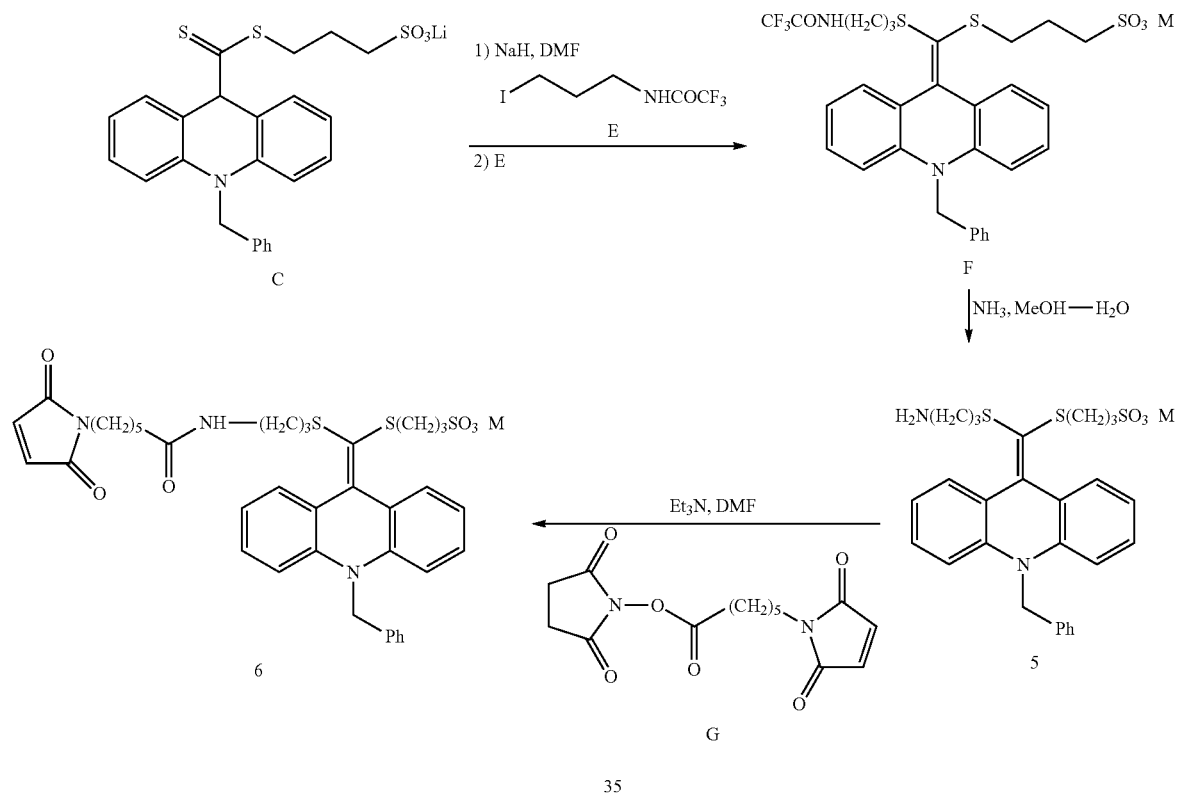

A mixture of dithioester C (1.32 g, 2.78 mmol) and NaH (60% in mineral oil, 0.114 g, 2.86 mmol) in 30 mL of anh. DMF was stirred under argon at room temperature for 4 hours. Compound E (1.014 g, 3.61 mmol) was then added in 10 mL of DMF. The mixture was stirred over night after which DMF was removed in vacuo. The residue was washed three times with 20 mL of ether giving 2.10 g of F.

Compound F (2.25 g) was dissolved in a mixture of 15 mL of 7 N NH3 in MeOH and 10 mL of 28% aqueous ammonia solution. After 3 days of stirring, solvents were removed under vacuum. The residue was washed with ether (3×50 mL) and recrystallized with H$_2$O/2-propanol, giving 1.20 g of 5.

To a suspension of 5 (0.300 g, 0.563 mmol) in 9.0 mL of dry DMF was added 1.20 mL of triethylamine. The mixture was stirred for 5 min, giving a slightly cloudy solution. To this was added 6-maleimidohexanoic NHS ester (G 0.260 g, 0.843 mmol). A clear solution as resulted in 5 min. After 16 hrs, DMF was removed under vacuum. The residue was washed with ether (4×30 mL), then dissolved in MeOH (2 mL) and precipitated with ether (50 mL). A 0.400 g yield of 6 was obtained as a yellowish foam-like solid. $^1$H NMR (400 MHz, CD$_3$OD): δ 1.26 (t, 11H), 1.49-1.58 (m, 6H), 1.90 (p, 2H), 2.08 (t, 2H), 2.68 (m, 4H), 2.80 (t, 2H), 3.00 (t, 2H), 3.15 (q, 6H), 3.42 (t, 2H), 5.28 (s, 2H), 6.73 (s, 2H), 6.85 (d, 2H), 6.96 (m, 2H), 7.07 (m, 4H), 7.18-7.25 (m, 3H), 7.83 (m, 2H) ppm.

Example 5

Additional Labeling Compounds 7-12

The preparation of other exemplary labeling compounds listed below was disclosed in U.S. Pat. No. 6,858,733.

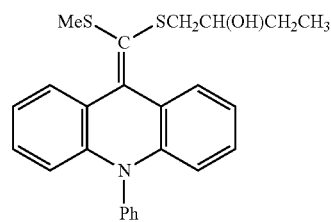

7

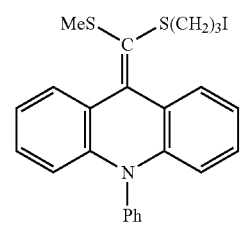

8

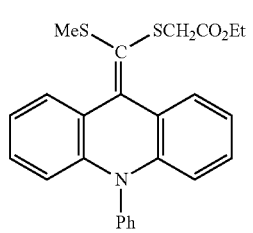

9

-continued

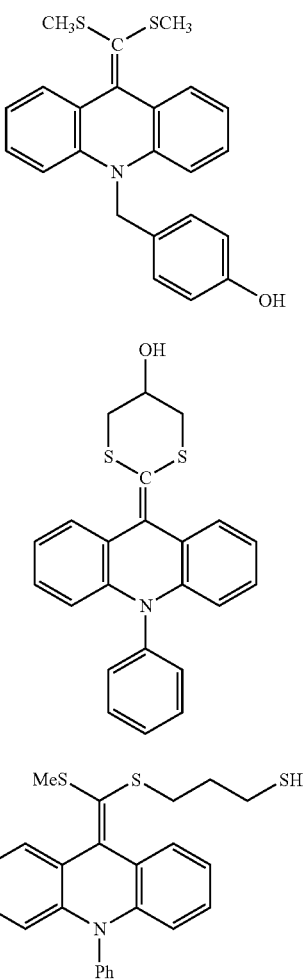

Example 6

Preparation of Acridan-labeled Antibody

The acridan labeling compound 3 of example 3 was used to label sheep anti-mouse IgG (H+L) (Jackson Immunoresearch). A solution of 0.24 mg of the antibody in 0.1 M borate buffer, pH 8.25 and compound 3 in DMF (10:1 molar ratio 3:antibody) in a volume of 500 μL was reacted for 15 min at room temperature and then at 4° C. over night. The solution was passed through a desalting column (BioRad) eluted with PBS buffer to remove unbound label. Labeled antibody along with any unreacted antibody was obtained by collecting 500 μL fractions.

The fractions were tested for the amount of labeled antibody by a chemiluminescent assay. A 1 or 10 μL aliquot was mixed with 50 μL of 0.4 M HCL+3.6% urea peroxide, followed by injection of 50 μL of 0.5 M NaOH in a tube in a Turner Designs TD-20e luminometer. The total integrated intensity from the burst of luminescence was measured from the time of injection. Those fractions showing chemiluminescence were retained. Fraction 8 contained the maximal amount of product.

Example 7

Preparation of Acridan-labeled BSA

The acridan labeling compound 3 of example 3 was used to label bovine serum albumin (BSA). A solution of 0.1 g of BSA in 500 μL of 0.1 M borate buffer, pH 8.25 and 42 μL of 23.4 mg compound 3/100 μL DMF (10:1 molar ratio 3:BSA) was reacted for 15 min at room temperature and then at 4° C. over night. The solution was passed through a desalting column (BioRad) eluted with PBS buffer to remove unbound label. Labeled BSA along with any unreacted BSA was obtained by collecting 500 μL fractions.

The fractions were tested for the amount of labeled BSA by the chemiluminescent assay in example 6. Those fractions showing chemiluminescence were retained. Fraction 7 contained the maximal amount of product.

Example 8

Preparation of Acridan Functionalized Microwells

White polystyrene 96-well microplates functionalized with carboxylic acid groups (Biosystems) are coupled with Compound 5 using EDC as coupling agent. A stock solution of Compound 5 in a 70:30 (v/v) solution of DMF and 0.1 M MES buffer, pH 4 is prepared. A 0.2 mL aliquot was added to each well of the plate that had been previously washed in MES buffer. EDC in MES buffer is added and the mixture reacted over night. The supernatant is removed and the wells washed sequentially 2× with water and 6× with methanol.

Example 9

Preparation of Acridan-Labeled Poly(methacrylate) Microparticles

Amberlite resin (IRP-64, 100-400 mesh, 2.50 g) was reacted with $SOCl_2$ at reflux for four hours. The reaction was cooled and the volatiles removed under vacuum. The beads were then suspended in 50 mL of $CH_2Cl_2$ to which 17.0 mL of triethylamine was added followed by 15.0 mL of ethylenediamine. The mixture was stirred under Ar over night. The particles were dispersed by addition of 100 mL of MeOH and then filtered. The filtered particles were washed with MeOH and $CH_2Cl_2$, and then air dried. The resulting particles weighed 2.80 g for a calculated $NH_2$ content of 2.86 mmol/g.

The ethylenediamine-modified particles, (100 mg) in 10 mL of anhydrous DMF, were stirred under Ar with 10 mg of Compound 2 at room temperature over night. The mixture was filtered and the particles washed with MeOH. After air-drying, the recovered functionalized particles weighed 102 mg.

In an alternate method, 2.50 g of Amberlite resin was converted to the acid chloride form by reaction with $SOCl_2$ as above, and then reacted with 4.32 g of N-hydroxysuccinimide in 50 mL of THF and 6.8 mL of triethylamine to prepare the NHS ester-functionalized particles. These were reacted with Compound 5 containing a free terminal $NH_2$ group to effect coupling.

Example 10

Conjugation of Acridan-Labeled Microparticles with Antibody

A 20 mg quantity of the Acridan-labeled Amberlite particles, containing unreacted terminal $NH_2$ groups, was further reacted with 102 mg of disuccinimidyl octanedioate, (~5 eq.) in 100 mL of anh. DMF for 15 min at room temperature. The particles were separated by centrifugation and washed with 10×1 mL of DMF. The resulting free NHS ester was coupled to sheep anti-mouse IgG (0.5 mL of a stock 1.8 mg/mL solution) in 0.1 M borate buffer, pH 8.5, 2 mM EDTA over night at 4° C. The reaction mixture was centrifuged at 13 k rpm and the supernatant removed. The particles were washed several times on a spin column with PBS+0.05% Tween-20.

The resulting antibody-labeled particles were blocked with BSA by incubation in 1.0 mL of blocking buffer (1% BSA, 1% sucrose in 1× PBS) at 37 C for 1 hour. The particles were washed with Tween-PBS wash buffer and stored in 1.0 mL of 1× PBS.

Example 11

Preparation of Acridan-Labeled Magnetic Microparticles

A stock solution of 4 mg of Compound 5 in a solution of 0.7 mL of DMF and 0.3 mL of 0.1 M MES buffer, pH 4 was prepared. A 0.1 mL aliquot was added to 50 mg of carboxylated polystyrene particles (Dynal Dynabeads M-270 carboxylic acid), which had been washed in MES buffer. The mixture was diluted with 0.67 mL of MES buffer and 0.23 mL of DMF. EDC (23 mg) was added and the mixture shaken over night. The supernatant was removed and the particles washed sequentially with 2×1 mL of water and 6×1 mL of MeOH and resuspended in 1 mL of MeOH.

The particles were tested for label incorporation. A 10 µL aliquot (containing ca. 0.5 mg) was added to 0.5 mL of water to prepare a 1 mg/mL stock. A 100 µL aliquot was reacted with an excess of HRP for 5 min. The particles were washed with 4×1 mL of water and then suspended in 1 mL of water. Trigger solution (10 µL) containing 25 mM tris, pH 8.0, 8 mM p-hydroxycinnamic acid, 1 mM EDTA, 0.2% Tween-20 and 0.1 M urea peroxide was injected and the flash of chemiluminescence recorded in a luminometer. A signal of 6040 RLU was observed compared to a blank of 18 RLU.

A 5 mg portion of particles was washed with 2×200 µL of 0.1 M MES buffer, pH 4 and then resuspended in 117 µL of MES buffer. Sheep anti-mouse IgG (0.15 mg from a stock 1.8 mg/mL solution) was added to the particles and the mixture was shaken for 30 minutes. EDC, 5 mg, was added and the mixture shaken for 4 hours. The supernatant was removed and the beads were washed with 3×500 µL of wash buffer (PBS+ 0.05% Tween-20). The particles were resuspended in 500 µL of blocking buffer (PBS+1% BSA+1% sucrose) and 5 mg of EDC, stirred for 15 min at room temperature and stirred at 4° C. over night. The supernatant was removed and the particles washed with 2×500 µL of wash buffer and resuspended in 1 mL of PBS.

Example 12

Microplate Immunoassay Using Labeled Capture Antibody

The product-containing fraction from the preparation of labeled antibody in example 6 was diluted 1:100 in PBS buffer. A 50 µL aliquot was added to each of 26 wells of a white polystyrene 96 well plate. The plate was agitated for 5 minutes at room temperature on an orbital shaker. The solution was removed and the wells washed three times with 1× PBS+0.05% Tween-20, removing all wash buffer after each step.

Sheep anti-mouse IgG F(ab$^1$)$_2$—HRP conjugate (Jackson Immunoresearch) was diluted 1:1.2×10$^6$ in a conjugate buffer comprising 2.5% BSA and 1% sucrose in 1× PBS. Alternatively, the conjugate could also be diluted in other matrices such as FBS.

Aliquots of diluted conjugate were dispensed into the 26 wells. IgG standards containing from 100 ng/mL-0.048 ng/mL were prepared by 2-fold dilution along with a 0 ng/mL solution in anti-IgG F(ab$^1$)$_2$—HRP conjugate solution. The standards and zero were dispensed into wells achieving a final volume 50 µL/well. The plate was incubated 1 hr at room temperature on the plate shaker.

A trigger solution was prepared containing 25 mM tris, pH 8.0, 8 mM p-hydroxy-cinnamic acid, 1 mM EDTA, 0.2% Tween-20 and 0.1 M urea peroxide.

The plate was transferred to a Luminoskan plate luminometer. Without removing the conjugate solution, luminescence was generated by sequentially injecting 100 µL of trigger solution, and reading the integrated intensity in each well for 5 seconds. A plot of the resulting assay is shown in FIG. 1. The assay allowed quantitation over the entire range tested with the lowest calibrator exceeding the signal of the zero+2 standard deviations of the zero.

Example 13

Microplate Immunoassay Unlabeled Capture Antibody and Labeled BSA

A 50 µL aliquot of unlabeled sheep anti-mouse IgG (H+L) 40 µg/mL of 1× PBS was added to coat each of 26 wells of a white polystyrene 96 well plate. The plate was agitated for 5 minutes at room temperature on an orbital shaker. The solution was removed and the wells washed three times with 1× PBS+0.05% Tween-20, removing all wash buffer after each step.

The product-containing fraction from the preparation of labeled BSA in example 7 was diluted in 50 µL/mL in PBS buffer+1% sucrose. A 100 µL aliquot was added to each of 26 wells of a white polystyrene 96 well plate. The plate was held for 1 hr at 37° C. The solution was removed and the wells washed three times with PBS+0.05% Tween-20, removing all wash buffer after each step.

Sheep anti-mouse IgG F(ab$^1$)$_2$—HRP conjugate was diluted 1:1.2×10$^6$ in a conjugate buffer comprising 1% BSA and 1% sucrose in 1× PBS. Aliquots of diluted conjugate were dispensed into the 26 wells. IgG standards containing from 100 ng/mL-0.048 ng/mL were prepared by 2-fold dilution along with a 0 ng/mL solution in anti-IgG F(ab$^1$)$_2$—HRP conjugate solution. The standards and zero were dispensed into wells achieving a final volume 50 µL/well. The plate was incubated 1 hr at room temperature on the plate shaker.

The plate was transferred to a Luminoskan plate luminometer. Without removing the conjugate solution, luminescence was generated by sequentially injecting 100 µL of trigger solution, and reading the integrated intensity in each well for 5 seconds. A plot of the resulting assay is shown in FIG. 2. The assay allowed quantitation over the entire range tested with the lowest calibrator exceeding the signal of the zero+2 standard deviations of the zero.

Example 14

Microparticle Immunoassay Using Labeled Magnetic Microparticles

Take 50 µg/reaction of Acridan and antibody co-labeled magnetic microparticles of example 11. The particles were washed three times with 1× PBS+0.05% Tween-20 and resuspended in sheep anti-mouse IgG F(ab$^1$)$_2$—HRP conjugate diluted 1:1.2×10$^6$ in 1× PBS buffer containing 1% BSA and 1% sucrose. The particle suspension was dispensed into 26 wells of a white polystyrene 96 well plate. IgG standards in sheep anti-mouse IgG F(ab$^1$)$_2$—HRP conjugate solution were prepared by 2-fold serial dilution to result in final concentrations of 100 ng/mL-0.048 ng/mL or 0 ng/mL in the wells. The respective standards and zero were dispensed into wells to make a final reaction volume of 50 µL/well. The plate was incubated for 1 hr at room temperature on a plate shaker.

The plate was transferred to a Luminoskan plate luminometer. Without removing the conjugate solution, luminescence was generated by sequentially injecting 100 µL of trigger solution, and reading the integrated intensity in each well for 5 seconds. A plot of the resulting assay allowed quantitation of IgG.

Example 15

Microparticle Immunoassay Using Labeled Amberlite Microparticles

Take 100 µg/reaction of acridan and antibody co-labeled Amberlite microparticles of example 10. The particles were washed three times with 1× PBS+0.05% Tween-20 and resuspended in sheep anti-mouse IgG F(ab$^1$)$_2$—HRP conjugate diluted 1:1.2×10$^6$ in 1× PBS buffer containing 1% BSA and 1% sucrose. The particle suspension was dispensed into 26 wells of a white polystyrene 96 well plate. IgG standards in sheep anti-mouse IgG F(ab$^1$)$_2$—HRP conjugate solution were prepared by 2-fold serial dilution to result in final concentrations of 100 ng/mL-0.048 ng/mL or 0 ng/mL in the wells. The respective standards and zero were dispensed into wells to make a final reaction volume of 50 µL/well. The plate was incubated for 1 hr at room temperature on a plate shaker.

The plate was transferred to a Luminoskan plate luminometer. Without removing the conjugate solution, luminescence was generated by sequentially injecting 100 µL of trigger solution, and reading the integrated intensity in each well for 5 seconds. A plot of the resulting assay allowed quantitation of IgG.

Example 16

Preparation of Acridan-Labeled Carboxyl-Modified Microparticles

Carboxylic acid-modified polystyrene 1 µm microparticles (Seradyn) having a carboxyl loading of 0.0282 meq/g were conjugated to Compound 5 by EDC coupling according to the procedure described in example 11. A 52.5 mg portion of particles (1.48 µmol COOH) was treated with 0.39 mg of 5 (0.74 µmol) to ensure that unreacted COOH groups remained. The free COOH groups were coupled to sheep ant-mouse IgG (1.48 µmol) by EDC coupling in pH 4 MES buffer. Unreacted antibody was removed by washing with Tween-PBS buffer using a spin column.

What is claimed is:

1. A kit for detecting an analyte in a sample comprising:
   (a) a solid support comprising thereon a chemiluminescent compound that is a peroxidase substrate and a first specific binding partner for said analyte; and
   (b) a peroxidase conjugated to a second specific binding partner.

2. The kit of claim 1 wherein the chemiluminescent compound comprises a chemiluminescent moiety and a linking moiety that links the chemiluminescent moiety to the solid support, wherein the chemiluminescent moiety is selected from luminol, isoluminol, aminobutylethylisoluminol, aminohexylethylisoluminol, 7-dimethylaminonaphthalene-1,2-dicarboxylic acid hydrazide, anthracene-2,3-dicarboxylic acid hydrazide, phenathrene-1,2-dicarboxylic acid hydrazide, pyrenedicarboxylic acid hydrazide, 5-hydroxyphthalhydrazide, 6-hydroxyphthalhydrazide, acridan esters, acridan thioesters, acridan sulfonamides, and groups of formula I wherein $R^1$, $R^2$ and $R^3$ are organic groups containing from 1 to 50 non-hydrogen atoms, and each of $R^4$-$R^{11}$ is hydrogen or a noninterfering substituent, wherein at least one of the groups $R^1$-$R^{11}$ comprises the linking moiety.

3. The kit of claim 1 wherein the chemiluminescent compound comprises a chemiluminescent moiety having formula I wherein $R^1$ and $R^2$ are independently substituted or unsubstituted alkyl, substituted or unsubstituted alkenyl, substituted or unsubstituted alkynyl, substituted or unsubstituted aryl, or substituted or unsubstituted aralkyl;
   $R^3$ is substituted or unsubstituted alkyl, substituted or unsubstituted alkenyl, substituted or unsubstituted alkynyl, substituted or unsubstituted aryl, substituted or unsubstituted aralkyl, alkoxyalkyl, carboxyalkyl or alkylsulfonic acid, wherein $R^3$ is optionally joined with $R^7$ or $R^8$ to form a 5 or 6-membered ring,
   $R^4$, $R^5$, $R^6$, $R^7$, $R^8$, $R^9$, $R^{10}$, and $R^{11}$ are independently hydrogen, substituted or unsubstituted alkyl, substituted or unsubstituted aryl, aralkyl, alkenyl, alkynyl, alkoxy, aryloxy, halogen, amino, substituted amino, substituted or unsubstituted carboalkoxy, carboxamide, cyano, or sulfonate, wherein pairs of adjacent groups of $R^4$, $R^5$, $R^6$, $R^7$, $R^8$, $R^9$, $R^{10}$, and $R^{11}$ are optionally joined to form a carbocyclic or heterocyclic ring system;
   and wherein at least one of the groups of $R^1$ to $R^{11}$ comprises a linking moiety that links the chemiluminescent moiety to the solid support.

4. The kit of claim 3 wherein at least one of $R^1$ to $R^3$ comprises the linking moiety, and wherein $R^4$, $R^5$, $R^6$, $R^7$, $R^8$, $R^9$, $R^{10}$, and $R^{11}$ are each hydrogen.

5. The kit of claim 3 wherein $R^1$ and $R^2$ are independently unsubstituted alkyl or alkyl substituted with 1 to 3 groups independently selected from carbonyl, carboxyl, tri($C_1$-$C_8$) silyl, $SO_3^-$, $OSO_3^{-2}$, glycosyl, $PO_3^-$, $OPO_3^{-2}$, halogen, hydroxyl, thiol, amino, quaternary ammonium, and quaternary phosphonium, and wherein $R^3$ is substituted or unsubstituted benzyl.

6. The kit of claim 2 wherein the linking moiety is selected from a bond, an atom, or a divalent or polyvalent of the group containing from 1 to about 50 non-hydrogen atoms selected from C, O, N, S, P, Si, B, and Se atoms, wherein the divalent or polyvalent group is selected from alkylene, arylene, alkenylene, ether, peroxide, ketone, ester, carbonate ester, thioester, amide, amine, amidine, carbamate, urea, imine, imide, imidate, carbodiimide, hydrazine, diazo, phosphodiester, phosphotriester, phosphonate ester, thioether, disulfide, sulfoxide, sulfone, sulfonate ester, sulfate ester, and thiourea groups.

7. The kit of claim 1 wherein the first specific binding partner, the second specific binding partner, or both are antibodies that bind to the analyte.

8. The kit of claim 1 wherein the first specific binding partner, the second specific binding partner, or both are binding proteins that bind to the analyte.

9. The kit of claim 1 wherein the first specific binding partner, the second specific binding partner, or both are nucleic acids that bind to the analyte.

10. The kit of claim 1 wherein the second specific binding partner is an analog of the analyte.

11. The kit of claim 1 wherein the chemiluminescent compound is covalently attached to the solid support.

12. The kit of claim 1 wherein the chemiluminescent compound is covalently attached to an auxiliary substance that is immobilized on the solid support.

13. The kit of claim 1 wherein the first specific binding partner is directly attached to the solid support.

14. The kit of claim 1 wherein the first specific binding partner is indirectly attached to the solid support.

15. The kit of claim 1 wherein the chemiluminescent compound is covalently attached to the first specific binding partner that is immobilized on the solid support.

16. The kit of claim 1 further comprising a trigger solution comprising a peroxide and a chemiluminescence enhancer compound selected from substituted or unsubstituted arylboronic acids, p-phenylphenol, p-iodophenol, p-bromophenol, p-hydroxycinnamic acid, p-imidazolylphenol, acetaminophen, 2,4,-dichlorophenol, 2-naphthol, 6-bromo-2-naphthol, 3-(N-phenothiazinyl)-propanesulfonic acid salts, 3-(N-phenoxazinyl)propanesulfonic acid salts, 4-(N-phenoxazinyl)butanesulfonic acid salts, 5-(N-phenoxazinyl)-pentanoic acid salts and N-methylphenoxazine.

17. The kit of claim 14 wherein the peroxide is selected from hydrogen peroxide, urea peroxide and perborate salts.

* * * * *